United States Patent [19]

Courneya

[11] Patent Number: 4,861,956
[45] Date of Patent: Aug. 29, 1989

[54] MICROWAVE/STEAM STERILIZER

[75] Inventor: Calice G. Courneya, Alexandria, Minn.

[73] Assignee: Magnetronics, Inc., Maple Grove, Minn.

[21] Appl. No.: 920,572

[22] Filed: Oct. 17, 1986

[51] Int. Cl.$^4$ ............................................. H05B 9/06
[52] U.S. Cl. ...................... 219/10.55 A; 219/10.55 F; 219/10.55 M; 219/10.55 R
[58] Field of Search ................. 219/10.55 A, 10.55 F, 219/10.55 R, 10.55 B, 10.55 M

[56] References Cited

U.S. PATENT DOCUMENTS

| | | | |
|---|---|---|---|
| 2,909,635 | 7/1957 | Haagensen | 219/10.55 F |
| 3,092,503 | 6/1963 | Gray. | |
| 3,215,539 | 11/1965 | Landy. | |
| 3,261,140 | 7/1966 | Long et al.. | |
| 3,430,022 | 2/1969 | Cougoule. | |
| 3,460,031 | 8/1969 | Evans et al.. | |
| 3,494,722 | 2/1970 | Gray. | |
| 3,494,724 | 2/1970 | Gray. | |
| 3,674,422 | 7/1972 | Gray. | |
| 3,743,480 | 7/1973 | Falk. | |
| 3,753,651 | 8/1973 | Boucher | 21/54 |
| 3,813,918 | 6/1974 | Moe. | |
| 3,926,556 | 12/1975 | Boucher. | |
| 4,159,406 | 6/1979 | Tate et al.. | |
| 4,210,795 | 7/1980 | Lentz. | |
| 4,303,818 | 12/1981 | Smith. | |
| 4,341,937 | 7/1982 | Staats. | |
| 4,424,430 | 1/1984 | Almgren et al.. | |
| 4,427,867 | 1/1984 | Dills. | |
| 4,446,349 | 5/1984 | Smith. | |
| 4,449,026 | 5/1984 | Satoh. | |
| 4,454,404 | 6/1984 | Zushi. | |
| 4,458,126 | 7/1984 | Dills et al.. | |
| 4,463,239 | 7/1984 | Miller. | |
| 4,464,554 | 8/1984 | Bakanowski | 219/10.55 F |
| 4,507,530 | 3/1985 | Smith | 219/10.55 B |

OTHER PUBLICATIONS

Acute Staphylococcal Infections in Rabbits Irradiated with 3-GHz Microwaves, S. Szmigielski, J. Jeljaszewicz, and Marzenna Wiranowska, Annals New York Academy of Sciences, pp. 305–311.
Microwave Sterilization, Michael D. Rohrer, Ronald A. Bulard, JADA, vol. 110, Feb. 1985, pp. 194–198.
Microwave Sterilization of Nitrous Oxide Nasal Hoods Contaminated with Virus, S. K. Young, D. C. Graves, M. D. Rohrer, and R. A. Bulard, Oral Surgery, Dec. 1985, pp. 581–585.
Lack of Microbial Genetic Response to 2.45-GHz CW and 8.5- to 9.6-GHz Pulsed Microwaves, S. K. Dutta, W. H. Nelson, C. F. Blackman, and D. J. Brusick, Journal of Microwave Power, 14(3), 1979, pp. 275–280.
The Effects of Microwave Radiation and Heat on Specific Mutants of Salmonella Typhimurium LT2, R. Dean Blevins, Rodger C. Crenshaw, Jr., Arthur E. Hougland, and Charles E. Clark, Radiation Research, 82, 511–517 (1980).

(List continued on next page.)

Primary Examiner—A. D. Pellinen
Assistant Examiner—Leon K. Fuller
Attorney, Agent, or Firm—Peterson, Wicks, Nemer & Kamrath

[57] ABSTRACT

In the most preferred form, a microwave/steam sterilizer and its method of operation are disclosed including a waveguide having a waveguide conduit including a terminal aperture located one quarter wavelength from the bottom of a water reservoir and including a series of subapertures spaced in the range of one quarter wavelength from each other. The waveguide further includes a mitered corner moveable to shift the microwave standing waves to communicate with the terminal aperture and/or the series of subapertures in response to conditions sensed in the working cavity. The waveguide and the walls of the working cavity are angled with respect to each other to avoid reflection of microwave energy back to the microwave energy generator. The sterilizer hydrates potential pathogens and subjects them to relatively uniform electromagnetic energy without arcing and without self-destruction of the microwave source by reflected microwave energy.

48 Claims, 3 Drawing Sheets

OTHER PUBLICATIONS

Microwave Oven Irradiation as a Method for Bacterial Decontamination in a Clinical Microbiology Laboratory Joan M. Latimer and John M. Matsen, *Journal of Clinical Microbiology*, vol. 6, No. 4, Oct. 1977, pp. 340–342.

The Microwave Oven: A Novel Means of Decontaminating Parasitological Specimens and Glassware, George A. Conder and Jeffrey F. Williams, *The Journal of Parasitology*, vol. 69, No. 1, Feb. 1983, pp. 181–185.

Effects of Heat Treatment on the Performance of Tryptose-Sulfite-Cycloserine Agar for Enumeration of Clostridium Perfringens, M. H. Brodsky and B. W. Ciebin, *Applied and Environmental Microbiology*, vol. 37, No. 5, May, 1979, pp. 1038–1040.

Mechanism of Lethal Action of 2,450-MHz Radiation on Microorganisms, G. R. Vela and J. R. Wu, *Applied and Environmental Microbiology*, vol. 37, No. 3, Mar. 1979, pp. 550–553.

Microwave Sterilization of Plastic Tissue Culture Vessels for Reuse, M. R. Sanborn, S. K. Wan, and R. Bulard, *Applied and Environmental Microbiology*, vol. 44, No. 4, Oct. 1982, pp. 960–964.

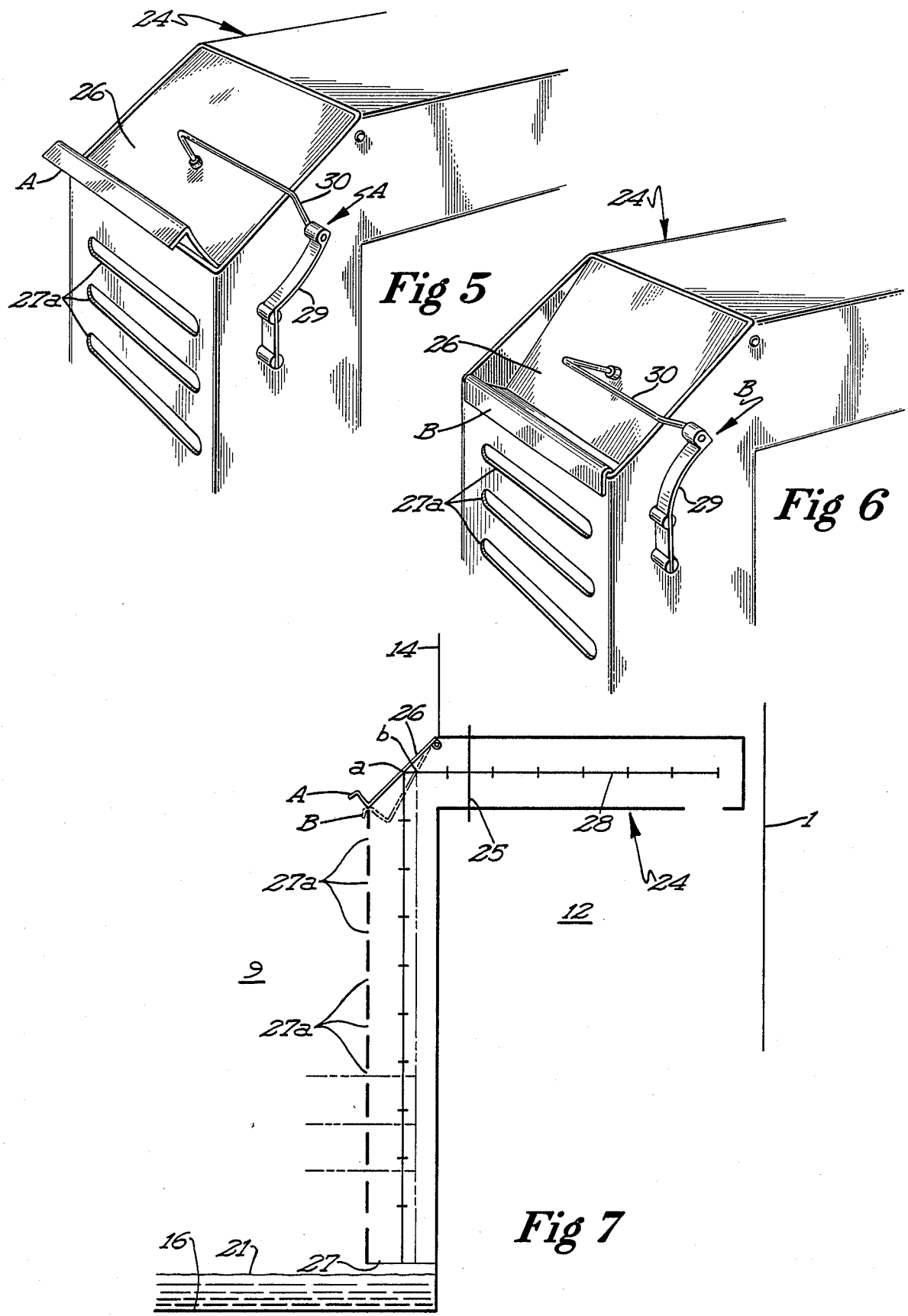

MICROWAVE/STEAM STERILIZER

BACKGROUND

This invention generally relates to a method and apparatus for sterilization of objects and goods, and particularly to a method and apparatus for sterilization in an atmosphere of gaseous water and electromagnetic energy in the microwave range at lower temperatures and shorter periods than those presently used to kill potential pathogens.

That mankind is continuing to evolve is a perceptive fact. As any species makes progress, it encounters new hazards and must adapt or gain the dubious distinction of being placed on a list. The brutal fact is that Mother Nature gives very few tests, but they are all finals.

The doctor, the dentist, and the restaurant owner would all assure you that Mother Nature would not give you her finals if they had a very fast, very sure, sterilizer. Sterilizers are no substitute for good housekeeping, but a sterilizer could insure that your doctor, your dentist, or your eating utensils didn't inoculate you. The vulnerability to hazards increases when you journey into the world. But, only because the scientific area of sterilizers has been neglected.

The continual increase in the mobility of mankind and the changes in lifestyles has heightened the need for a commonplace practice to prevent the inoculation of gross segments of the population with potential pathogens. Sterile practices have expanded from the surgical sight to other areas of potential inoculation but not nearly at a pace adequate to isolate pathogenic outbreaks. The primary reason for the failure of sterile practices to keep pace with the expanding need is a complex combination of factors including: the reluctance to admit that a problem exists, the current cumbersome solutions to the problem, the insensitivity of the regulatory agencies, cost, and the absence of a viable alternative to current cumbersome processes.

At present, the old fashioned steam sterilizer is still the workhorse employed by those concerned with sterile practices. With each problem encountered, the art of sterile practice has added a solution to the process in order to solve that problem. Autoclaves require that low heat transfer air be removed from the cavity. The solution to this problem has been to add an evacuation cycle or a repetitive gravity displacement cycle to remove the air. Another problem with autoclaves is that the sterilized load is wet after being sterilized. Wet loads provide a ready avenue for reinfestation by potential pathogens. The solution to this problem has been to add a drying cycle to the autoclave. By adding solutions to solve these inherent problems, the cycle time of the autoclave has lengthened the total time from cycle to cycle. Slow, cumbersome operation has limited the autoclave operation to the necessary only. Thus, these autoclaves are slow, expensive pressure vessels which require regular inspections from several agencies. In addition, the autoclave is destructive to many plastics.

For more than ten years, microwave energy has been known to cause near instant death to all virus and bacteria. Yet, there is not a microwave sterilizer on the market for three major reasons, namely: 1. the inability of microwave energy to kill dry spores; 2. the inability of the science to create a uniform energy field; and 3. the tendency to self destruct from its own energy.

It is, therefore, an object of this invention to provide a novel chamber for sterilizing eating utensils, laboratory instruments, medical and dental tools, and other goods through the application of water vapor and microwave energy.

It is further an object of this invention to provide such a novel sterilizing chamber which sterilizes at far lower general temperatures than those encountered in the conventional autoclave or dry sterilizers to allow for the sterilization of numerous low melting point materials.

It is further an object of this invention to provide such a novel sterilizing chamber which sterilizes at a faster general rate than those encountered in the conventional autoclave or dry sterilizers.

It is further an object of this invention to provide such a novel sterilizing chamber having differential temperature points to control the location of water quantities within the sterilizer chamber through selective condensation to prevent the potential for recontamination of the sterilized load along wet paths in the load.

It is further an object of this invention to provide such a novel sterilizing chamber which forms a synergy of steam and microwave energy to cause rapid sterilization.

It is further an object of this invention to provide such a novel sterilizing chamber which causes rapid sterilization with or without the requirement of a pressure chamber.

It is further an object of this invention to provide such a novel sterilizing chamber which prevents the self-destruction of the microwave source by trapping reflected energy in a parallel load.

It is further an object of this invention to provide such a novel sterilizing chamber which sterilizes objects without destruction of their sharp working points or edges by arcing.

It is further an object of this invention to provide such a novel sterilizing chamber which alters the standing waves in the sterilizing chamber in response to the condition of the working covity and/or load to be sterilized.

These and further objects and advantages of the present invention will become clearer in light of the following detailed description of an illustrative embodiment of this invention described in connection with the drawings.

DESCRIPTION OF THE DRAWINGS

The illustrative embodiment may best be described by reference to the accompying drawings where:

FIGS. 5 and 6 show enlarged perspective views of the microwave shifting apparatus of the microwave/steam sterilizer of FIG. 1.

FIG. 7 shows a diagrammatic sectional view of the waveguide of the microwave/steam sterilizer of FIG. 1 for the purpose of illustrating the shifting of the standing wave.

Figure 1:
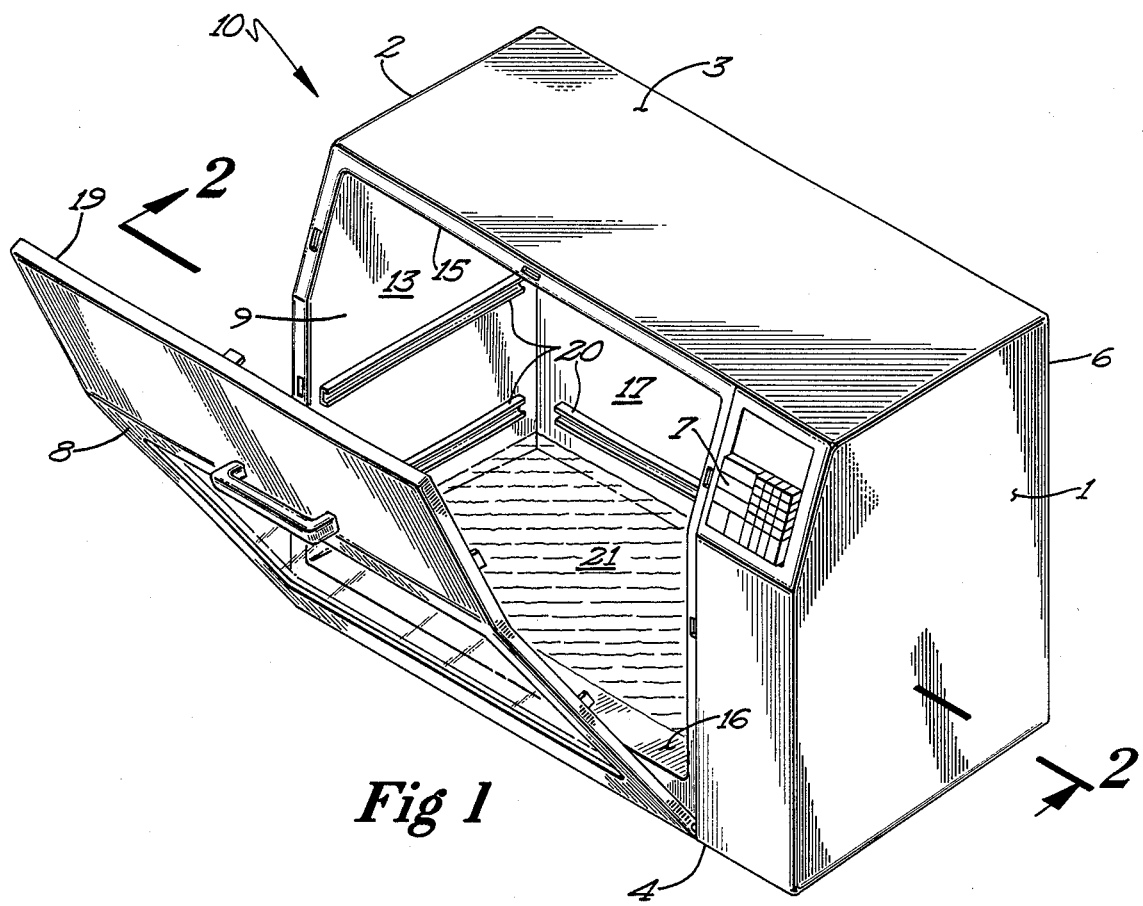
FIG. 1 shows a front perspective view of a microwave/steam sterilizer according to the preferred teachings of the present invention.

All figures are drawn for ease of explanation of the basic teachings of the present invention only; the extensions of the Figures with respect to number, position, relationship, and dimensions of the parts to form the preferred embodiment will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

Where used in the various figures of the drawings, the same numerals designate the same or similar parts. Furthermore, when the terms "top", "bottom", "upper", "lower", "first", "second", "front", "rear", "end", "edge", "inside", "outside", and similar terms are used herein, it should be understood that these terms have reference only to the structure shown in the drawings as it would appear to a person viewing the drawings and are utilized only to facilitate describing the invention.

DESCRIPTION

Figure 2:
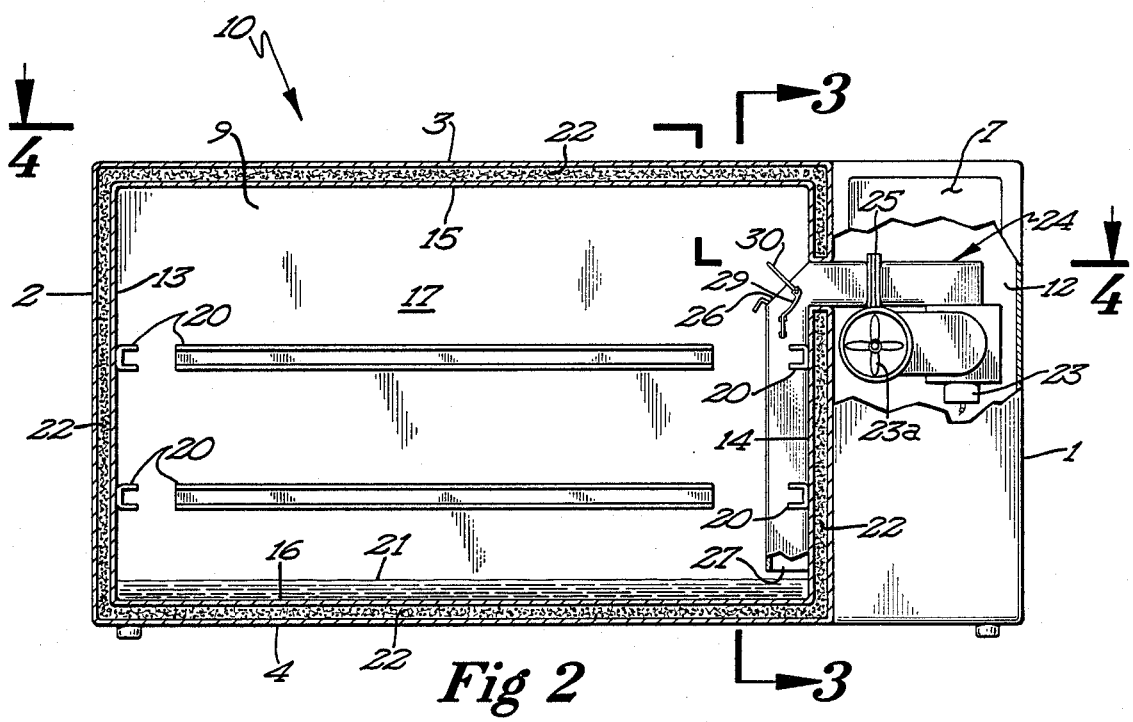
FIG. 2 shows a front sectional view of the microwave/steam sterilizer of FIG. 1 taken along line 2—2 of FIG. 1.
Figure 3:
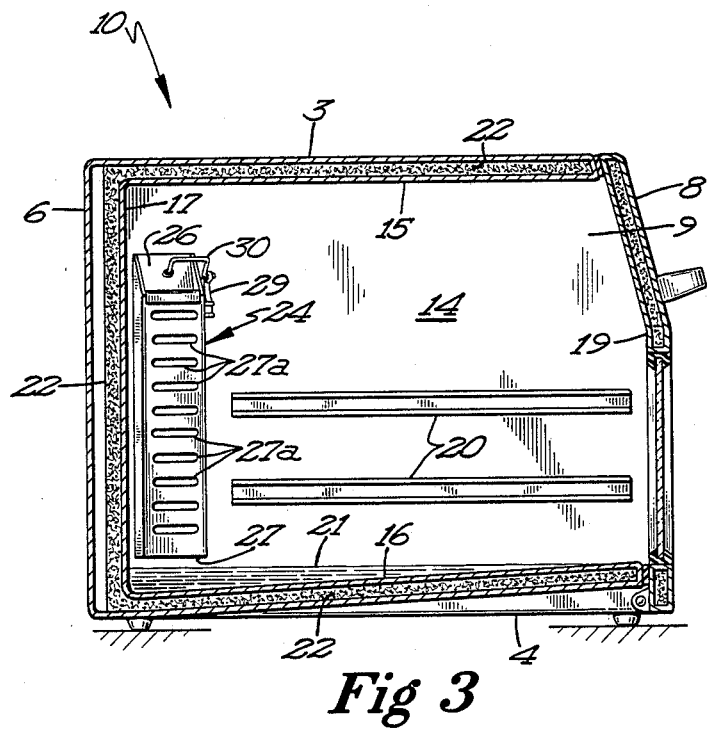
FIG. 3 shows a side sectional view of the microwave/steam sterilizer of FIG. 1 taken along line 2—2 of FIG. 2.
Figure 4:
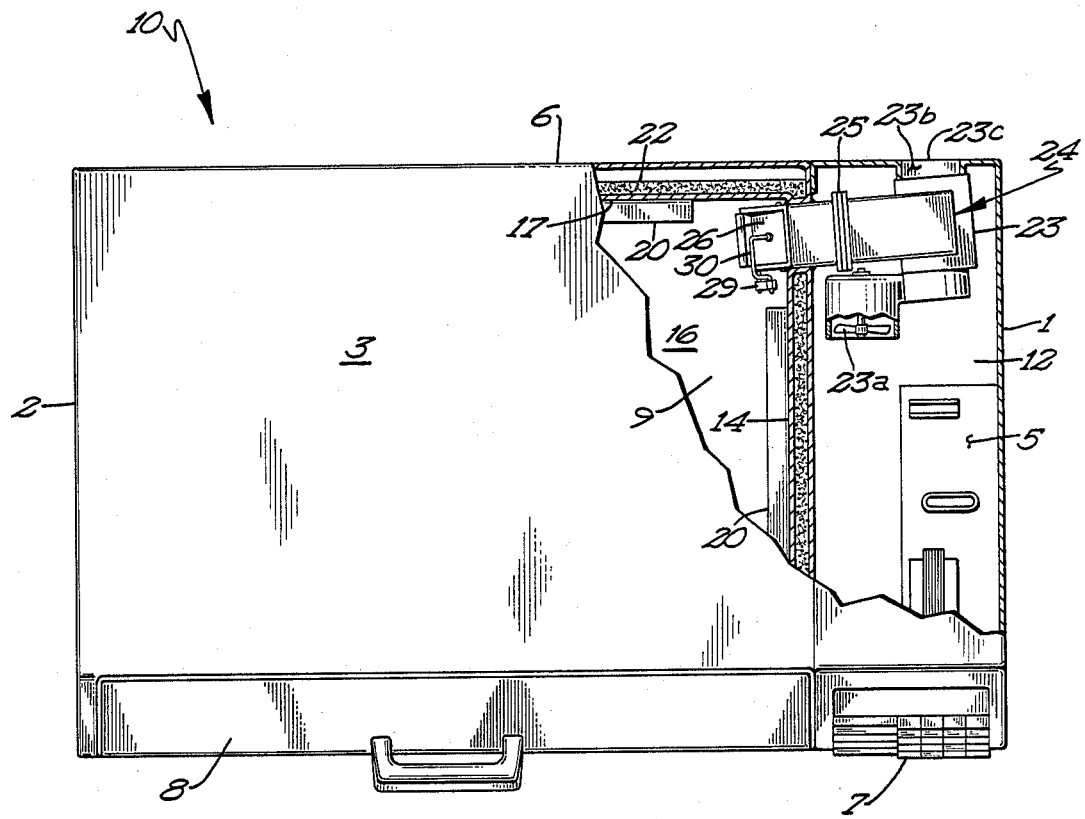
FIG. 4 shows a top sectional view of the microwave/steam sterilizer of FIG. 1 taken along line 4—4 of FIG. 2.

FIGS. 1 through 7 show a microwave/steam sterilizer 10 according to the preferred form of the teachings of the present invention. The outer cabinet comprising six walls including side walls 1 and 2, upper and lower walls 3 and 4, one rear wall 6 and a front wall partly formed by control panel 7 and partly formed by a hinged door 8. The cabinet, thus formed, is divided generally into a working cavity 9 and a control cabinet or cavity 12. Working cavity 9 is an inner cabinet comprising six conductive walls including side walls 13 and 14, upper and lower walls 15 and 16, one rear wall 17 and a front wall which is the inner face 19 of the hinged door 8.

In the usual manner, the door wall of working cavity 9, through which goods and objects to be sterilized are introduced into working cavity 9, contains the usual high frequency seals and electrical interlocks, not specifically shown.

Shelf support rails 20 are fastened to the two side walls 13 and 14 and the rear wall 17 of the working cavity 9. The lower wall 16 is sloped downward toward the rear wall 17 to form a shallow reservoir for water 21. The working cavity is encased in a layer 22 of thermal insulating material to confine thermal energy to the working cavity 9.

The energy source for working cavity 9 is a magnetron 23 which is mounted to the waveguide 24 in the control cabinet 12 and is cooled by fan 23a through appropriate ducting 23b and out of the control cabinet 12 through exit 23c. The center frequency of the magnetron 23 is 2450 MHz at its output when powered by a suitable power supply 5 housed in control cabinet 12. Magnetron 23 generates electromagnetic waves of a length near 4.82 inches (12.24 cm) which are conducted away from the magnetron 23 by the waveguide 24, through the vapor barrier 25, and are reflected downward by the mitered corner 26 toward the terminal aperture 27 and thence primarily to the water 21.

The vapor barrier 25 is a microwave transparent material such as quartz or other commercially available material marketed for that purpose which acts as a window to permit the passage of microwave energy and prevent the passage of vapors from the working cavity 9 and thence back through the waveguide 24 to the magnetron 23. This vapor barrier should be located transverse to the cross section of waveguide 24 and within control cabinet 12, at a point in nearest proximity to insulation layer 22, to prevent the formation of a cool spot which would serve to condense vapors. The selection of the material forming vapor barrier will then depend upon its transparency to microwave and its imperviousness to vapor and in addition will depend upon the pressure of operation of working cavity 9 above or below atmospheric pressure.

The general electrophysical construction of the waveguide 24 is dictated by the wavelength of the energy applied by the magnetron 23. The combination of the wavelength of the energy applied by the magnetron 23 and the electrophysical construction of the waveguide 24 results in a steady state standing wave of the energy which the waveguide conducts into the work cavity 9. Alterations in the electrophysical construction of the waveguide 24 will result in a new combination and a new standing wave. This can best be understood by reviewing FIG. 7 where the marked line 28 down the centerline of the waveguide 24 is segmented in one quarter wavelengths which depict the steady state standing wave. The marked line 28 encounters point a of the mitered corner 26 and is reflected toward the terminal aperture 27. When the mitered corner 26 is in position A, the marks on marked line 28 do not communicate substantially with the location of the subapertures 27a. When the mitered corner 26 is caused to move to position B, the marks on marked line 28 encounters point b of the mitered corner 26 and show substantial communication with subapertures 27a thereby conducting microwave energy into the working cavity 9.

The mitered corner 26 may be statically set to accomplish a split in the microwave energy between the terminal aperture 27 and subapertures 27a or the mitered corner 26 may be hinged and caused to be set between positions A and B in response to the temperature of the working cavity 9 or in response to the temperature of goods and objects to be sterilized or in response to a compound of those temperatures. Sterilizer 10 according to the teachings of the present invention includes suitable provision for causing a shift in position of mitered corner 26. One such example can be seen more clearly in FIG. 5 and FIG. 6 where the position A and B are influenced by a temperature sensitive element 29 attached to that portion of the waveguide 24 which extends into the working cavity 9 and is in mechanical communication with mitered corner 26 by linkage 30. Specifically, temperature sensitive element 29 in its most preferred form is a bimetalic strip which is prepositioned and selected to complete the shift of mitered corner 26 from position B as the chamber temperature approaches 210° F. (98.9° C.). Likewise, mitered corner 26 could be shifted utilizing a snap action device to accomplish switching at a threshold temperature of chamber 9 or the load temperature by way of attaching a thermopile to linkage 30 or a compound combination of both temperatures. Similarly, mitered corner 26 could be shifted in response to chamber pressure and/or load pressure such as objects in a sealed bag. Again, shifting could be the result of chamber pressure and/or load pressure and chamber and/or load temperature.

It can be seen that when mitered corner 26 is in position A, the preponderance of microwave energy is directed out through the terminal aperture 27 and into the water 21 which forms steam to heat the working cavity 9. As the steam conducts heat to the working cavity 9, it also influences the temperature sensitive element 29 to change the angle of mitered corner 26 thereby causing a shift in the standing wave toward communication with subapertures 27a and into the working cavity 9 above the water 21. When the mitered corner 26 is caused to move toward position B, the microwave energy is directed more toward subapertures 27a which communicate with the goods and objects to be sterilized in working cavity 9.

As microwave energy is directed into the working cavity 9, steady state standing waves are generated within the working cavity 9. When there is any change in the geometry of the working cavity 9 and/or the applied electromagnetic waves, a new pattern of steady state standing wave is generated. With the above disclosure, it can be understood that the influence of temperature in the working cavity 9 would continually cause the standing wave to change from the influence of microwave energy out of a single terminal aperture 27 to the multiplicity of subapertures 27a or a combination thereof. It can be further understood that a great multiplicity of standing waves will be generated in the working cavity by the transmission of microwave energy through the multiplicity of subapertures 27a.

Microwave energy is reflected by electrically conductive surfaces such as the walls of the working cavity 9 and metallic goods or objects to be sterilized. This reflected microwave energy can be conducted in the reverse direction through the terminal aperture 27 and subapertures 27a into the waveguide 24 and back to the magnetron 23 causing it to self-destruct. The water 21 acts as a trap to minimize the entrance of reflected energy into terminal aperture 27. The proximity of terminal aperture 27 to the bottom wall 16 of working cavity 9 will influence the effectiveness of the water as a trap. The optimum proximity of terminal aperture 27 to the bottom wall 16 of working cavity 9 has been found to be one quarter wavelength of the applied microwave energy. The proximity of the level of water 21 to the terminal aperture 27 has been found to be as near to the terminal aperture 27 as is practical, allowing for the greatest depth of water 21. In the most preferred form, terminal aperture 27 may well extend below the surface of water 21 as long as the one quarter wavelength distance is maintained between terminal aperture 27 and bottom wall 16 of working chamber 9. Thus, steam generated enters working cavity 9 through subapertures 27a in the most preferred form.

Microwave energy reflected back into subapertures 27a is of lesser influence on the self-destruction of the magnetron 23 because of the reduced capacity of microwave energy transmission associated with each subaperture 27a and the alignment of the waveguide 24 with respect to the walls of the working cavity 9. This alignment can best be understood from FIG. 4 where waveguide 24 is intentionally misaligned with respect to the rear wall 17 to avoid the first order reflection of microwave energy back from side wall 13 and thence back through subapertures 27a. Microwave energy is subject to the laws of incidence and reflection, therefore, the angle of misalignment of waveguide 24 must be adequate to avoid the coincidence of first order reflection of microwave energy with the subapertures 27a. In addition, the angle of lower wall 16 of working cavity 9 would tend to correct the angle of reflection out of and into terminal aperture 27 as it relates to reflections off side wall 13 of working cavity. Other manners of putting the second order reflected energy from terminal aperture 27 into the same position as the first order reflections from subapertures 27a which would avoid coincidence with terminal aperture 27 may be utilized with the teachings of the present invention.

Now that the construction of sterilizer 10 according to the preferred teachings of the present invention has been explained, the basic operation and subtle features of sterilizer 10 according to the teachings of the present invention can be set forth and appreciated. In order to cause the death of potential pathogens, environmental changes must be made at a rate to exceed their adaptability. In a steam sterilizer, it is the general practice to eliminate or reduce the amount of air present because air acts as an intercessor for energy transfer from the heat source to the potential pathogen and that transfer rate is slower than steam. Various potential pathogens do not die at atmospheric pressure steam temperatures. It is those potential pathogens which hamper progress in sterilization.

Microwave energy can be applied to potential pathogens directly without the need of an intercessor, thereby without being limited by the properties of the intercessors. Microwave energy is understood to be a coherent electromagnetic wave and, as such, readily aligns to form standing waves which create fixed areas of high and low energy density. To affect the reproductive capabilities of a mass of micro-organisms in a uniform manner, a relatively uniform electromagnetic exposure must be applied. Sterilizer 10 according to the teachings of the present invention creates the effect of uniformity by subjecting the mass of micro-organisms to a uniform average of extremes.

As substances come under the influence of electromagnetic energy, they will react to that energy in one of three ways: 1) It will pass that energy through itself much like a window; 2) It will reflect that energy; or 3) It will trap or absorb that energy and convert it to heat. The reaction of a given substance to the influence of a given electromagnetic energy depends upon the compatibility of the electrophysical properties of both. As an example, water readily absorbs electromagnetic energy when that electromagnetic energy is caused to change direction at/or near a rate of 2,450 MHz. This rate falls within the frequencies reserved for the purpose of changing wave energy into heat energy. All of the electromagnetic waves which fall into that prescribed reservation are called microwaves.

Microwave energy can be applied to a potential pathogen at a rate sufficient to cause their internal water to become pressurized steam. The internal pressure of the potential pathogen can be catastrophic because of its thermal effect or cause physical destruction of that potential pathogen by rupture, much like a kernel of popcorn.

The internal water quantity which must be present in a potential pathogen to cause its death when placed under the influence of a microwave source is not a specific quantity. Each spore, for example, will hydrate above the threshold of dormancy when in an atmosphere of water at a vapor pressure above the osmotic pressure of the spore. As the spore hydrates, it becomes a better receptor of microwave energy. When the hydrated spore absorbs microwave energy, the temperature of the spore increases and tends to drive the water out of the spore, thereby lessening its vulnerability to microwave energy. The key to killing potential pathogens is the rate and sequence of the application of water and microwave energy. The proper sequence is the application of water at a vapor pressure adequate to allow dry potential pathogens to hydrate to a degree above their dormancy and then apply a microwave energy field of an intensity adequate to create lethal heat.

The absolute quantity of water required to hydrate a given strain of spore is not a constant. Sterilizer 10 according to the teachings of the present invention provides an adequate availability of water, as steam, to allow the dry spore to hydrate without flooding with excess water. Excess water serves as a coolant and prevents the formation of super-heated steam internally within the spores. Photomicrographs indicate that hydrated spores act very much like popcorn under the influence of microwave energy. This is understood to occur because the water absorbed from the steam and into the spore, becomes a primary receptor of microwave energy making the spore vulnerable. Vegetative pathogens have an existing adequate quantity of water present in them to insure their vulnerability to microwave energy without the addition of steam.

Microwave energy sources are capable of receiving energy into their outlet, as well as broadcasting energy out of their outlet. The applied energy to a microwave source must be adequate to maintain the internal conditions required for efficient broadcast from its outlet. These conditions are very narrow and can be easily upset by minor changes which can destroy the source. When microwave energy is generated by a source, that energy must have a load into which it is absorbed or it will be reabsorbed by the source. When microwave energy is generated and carried away toward a load, it can be reflected back into the source. Both of these conditions are out of the narrow operational conditions of the source and can result in its self-destruction.

According to the teachings of the present invention, potential pathogens are subjected to steam and microwave energy by sterilizer 10. The proportion of each is variable and controlled, which results in a synergy of both forces. Certain dry spores will not be killed by microwave energy alone, nor will they die in a practical length of time by the application of atmospheric pressure steam. When both forces are employed they perish quickly.

Sterilizer 10 according to the teachings of the present invention creates working cavity 9 with a pool of deionized water located very near the outlet of the waveguide 24 which transports microwave energy into working cavity 9. This pool of water acts as a ready receptor of microwave energy to keep the microwave energy source operating at peak efficiency. This water is also the source of the required steam and it acts as a reflected energy trap to prevent the microwave energy source from destroying itself in the presence of large metal loads. The steam generated from the water is rapidly absorbed by dry spores which makes them vulnerable to death by direct microwave energy. In the conventional dry microwave chambers, metallic objects and, more specifically, sharp or pointed objects will arc and spark which damages them and causes harm to the microwave energy source. In working cavity 9 of sterilizer 10 according to the teachings of the present invention, the water vapor keeps those electrical charges so low that arcing and sparking are overcome.

Sterilizer 10 according to the teachings of the present invention is unaffected by the presence of air in working cavity 9 and the load does not get wet in the classic sense. The steam is attracted to the dry spores by the osmotic pressure of the dry spore while excess steam is preferentially attracted to the coolest area in the chamber, namely the chamber walls. This results in dry sterile loads without a drying cycle. The only post treatment required with sterilizer 10 according to the teachings of the present invention is to allow the sterile load to cool. Therefore, the cycle time is at a minimum. An example of the cycle time difference is that a fifty minute autoclave cycle time would translate to a six minute cycle time from load to load on a continuous repetitive basis for sterilizer 10 according to the teachings of the present invention.

As described above, the combination microwave/-steam sterilizer 10 according to the teachings of the present invention accomplishes hydration, sterilization and drying of goods and objects as an inherent benefit from the sequence of operation controlled by the temperature of two alternate influences or in combination.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. Microwave waveguide structure for use in conducting microwave energy in a path intermediate a microwave energy generator and a working cavity comprising, in combination: a first waveguide conduit having a first end and a second end; a second waveguide conduit having a first end, with the first and second waveguide conduits being connected together by their first ends at an intersection generally perpendicularly to each other; with the first waveguide conduit extending from the microwave energy generator into the working cavity and with the second waveguide conduit located in the working cavity, with the microwave energy generator applying the microwave energy adjacent to the second end of the first waveguide conduit resulting in standing waves; means in the second waveguide conduit for introducing microwave energy generated by the microwave energy generator into the working cavity; and means located at the intersection of the first and second waveguide conduits for communicating the microwave energy from the first waveguide conduit continuously into the second waveguide conduit and for selectively shifting the standing waves of the microwave energy in the second waveguide conduit.

2. The microwave waveguide structure of claim 1 wherein the second waveguide conduit has a second end; wherein the introducing means comprise, in combination: a terminal aperture formed in the second end of the second waveguide conduit, and a series of subapertures located along the second waveguide conduit and spaced one quarter wavelength of the microwave energy generated by the microwave energy generator; and wherein the communicating and shifting means shifts the standing waves of the microwave energy in the second waveguide conduit between a first position to not communicate substantially with the series of subapertures and a second position to substantially communicate with the series of subapertures.

3. The microwave waveguide structure of claim 2 wherein the communicating and shifting means comprises means for shifting the standing waves of the microwave energy between the first and second positions in response to the temperature in the working cavity.

4. Microwave waveguide structure for use in conducting microwave energy in a path intermediate a microwave energy generator and a working cavity comprising, in combination: a first waveguide conduit having a first end and a second end; a second waveguide conduit having a first end, with the first and second waveguide conduits being connected together by their first ends at an intersection generally perpendicularly to each other; with the first waveguide conduit extending from the microwave energy generator into the working cavity and with the second waveguide conduit located in the working cavity, with the microwave energy generator applying the microwave energy adjacent to the second end of the first waveguide conduit resulting in standing waves; means in the second waveguide conduit for introducing microwave energy generated by the microwave energy generator into the working cavity; and a mitered corner at the intersection of the first and second waveguide conduits movable between a first position and a second position for communicating the microwave energy from the first waveguide conduit into the second waveguide conduit and for shifting the standing waves of the microwave energy in the second waveguide conduit.

5. The microwave waveguide structure of claim 2 further comprising, in combination: a shallow reservoir for water, with the reservoir having a bottom, with the terminal aperture located substantially one quarter wavelength of the applied microwave energy from the bottom of the reservoir.

6. The microwave waveguide structure of claim 5 wherein the terminal aperture extends below the water in the reservoir forcing steam generated by the applied microwave energy to enter the working cavity through the series of subapertures in the second waveguide conduit.

7. The microwave waveguide structure of claim 1 wherein the working cavity has at least a first wall and wherein; the introducing means guides the microwave energy into the working cavity at the wall of the working cavity at a nonperpendicular angle to prevent first order reflection of the microwave energy from re-entering the introducing means.

8. The microwave waveguide structure of claim 2 wherein the working cavity includes a wall opposite to the series of subapertures, with the series of subapertures being misaligned in a nonparallel relation with respect to the wall opposite to the series of subapertures to avoid the coincidence of first order reflection with the series of subapertures.

9. Apparatus comprising, in combination: means for generating electromagnetic waves; a working cavity; means for sensing a condition within the working cavity; and means for conducting the electromagnetic waves from the generating means into the working cavity resulting in standing waves and for shifting the standing waves in response to the condition within the working cavity sensed by the sensing means.

10. The apparatus of claim 9 wherein the conducting and shifting means includes a terminal aperture and at least one subaperture; and wherein the conducting and shifting means shifts the standing waves between a first position to substantially communicate with the terminal aperture and a second position to substantially communicate with the subaperture.

11. The apparatus of claim 10 further comprising, in combination: means separate from the load subjected to the electromagnetic waves in the cavity for trapping reflected electromagnetic waves not absorbed by the load for preventing self-destruction of the electromagnetic wave generating means comprising means for absorbing the electromagnetic waves located adjacent to the terminal aperture.

12. The apparatus of claim 11 wherein the absorbing means comprises a reservoir for water.

13. The apparatus of claim 12 wherein the absorbing means is supported on a lower wall of the working cavity, with the terminal aperture located in the range of one quarter wavelength of the generated electromagnetic waves from the lower wall of the working cavity.

14. The apparatus of claim 13 wherein the terminal aperture extends below the water of the reservoir forcing water vapor to enter the working cavity through the subaperture.

15. The apparatus of claim 13 wherein the working cavity further includes a wall opposite to the subaperture, with the subaperture being misaligned in a nonparallel relation with respect to the wall opposite to the subaperture to avoid the coincidence of first order reflection with the subaperture.

16. The apparatus of claim 15 further comprising, in combination: a series of subapertures spaced in the range of one quarter wavelength of the electromagnetic waves generated by the generating means.

17. The apparatus of claim 10 wherein the working cavity includes a lower wall, with the terminal aperture located in the range of one quarter wavelength of the generated electromagnetic waves from the lower wall of the working cavity.

18. The apparatus of claim 9 wherein the condition sensing means comprises, in combination: means for sensing temperature in the working cavity.

19. The apparatus of claim 18 wherein the temperature sensing means comprises a bimetallic strip located in the working cavity.

20. The apparatus of claim 9 wherein the conducting and shifting means comprises, in combination: a first waveguide conduit having a first end and a second end; a second waveguide conduit having a first end and a second end; with the first and second waveguide conduits being connected together by their first ends at an intersection generally perpendicularly to each other; with the first waveguide conduit extending from the electromagnetic wave generating means into the working cavity and with the second waveguide conduit located in the working cavity, with the electromagnetic wave generating means introducing the electromagnetic waves adjacent to the second end of the first waveguide conduit; means in the second waveguide conduit for introducing the electromagnetic waves into the working cavity; and means located at the intersection of the first and second waveguide conduits for continuously communicating the electromagnetic waves from the first waveguide conduit into the second waveguide conduit and for selectively shifting the standing waves in response to the condition within the working cavity sensed by the sensing means.

21. The apparatus of claim 20 wherein the communicating and shifting means comprises a mitered corner at the intersection of the first and second waveguide conduits movable between a first position and a second position by the sensing means.

22. The apparatus of claim 21 wherein the condition sensing means comprises, in combination: means for sensing temperature in the working cavity.

23. The apparatus of claim 22 wherein the temperature sensing means comprises, in combination: a bimetallic strip located in the working cavity; and a linkage between the bimetallic strip and the movable mitered corner.

24. The apparatus of claim 20 wherein the introducing means comprise, in combination: a terminal aperture formed in the second end of the second waveguide conduit; and a series of subapertures located along the second waveguide conduit and spaced in the range of one quarter wavelength of the electromagnetic waves generated by the generating means.

25. Microwave apparatus comprising, in combination: a microwave energy generator; a working cavity for receiving the microwave energy, with the working cavity having at least a first wall; means for guiding of the microwave energy from the microwave energy generator into the working cavity at the wall of the working cavity at a nonperpendicular angle to the wall to prevent first order reflection of the microwave energy from re-entering the guiding means.

26. The microwave apparatus of claim 25 wherein the guiding means includes an aperture for introducing the microwave energy into the working cavity, with the aperture misaligned in a nonparallel relation with respect to the wall of the cavity.

27. Microwave apparatus comprising, in combination: a microwave energy generator; a working cavity for receiving a load for subjection to the microwave energy; means for guiding the microwave energy into the working cavity having a terminal aperture; means for trapping reflected microwave energy not absorbed by the load for preventing re-entry of the reflected microwave energy from the working cavity through the terminal aperture for preventing self-destruction of the microwave energy generator comprising means located adjacent the terminal aperture for absorbing the microwave energy.

28. The microwave apparatus of claim 27 wherein the guiding means further comprises, in combination: at least one subaperture for conducting microwave energy into the working cavity generally perpendicularly from the microwave energy conducted into the working cavity by the terminal aperture.

29. The microwave apparatus of claim 28 wherein the subaperture is misaligned in a nonparallel relation with respect to the working cavity to avoid first order reflection of microwave energy back through the subaperture.

30. The microwave apparatus of claim 28 wherein the guiding means comprises, in combination: a first waveguide conduit having a first end and a second end; a second waveguide conduit having a first end and a second end; with the first and second waveguide conduits being connected together by their first ends at an intersection generally perpendicularly to each other; with the first waveguide conduit extending from the microwave energy generator into the working cavity and with the second waveguide conduit located in the working cavity, with the microwave energy generator applying the microwave energy adjacent to the second end of the first waveguide conduit, with the terminal opening formed in the second end of the second waveguide conduit, with the subaperture being formed intermediate the first and second ends of the second waveguide conduit; and means located at the intersection of the first and second waveguide conduits for continuously communicating the microwave energy from the first waveguide conduit into the second waveguide conduit.

31. The microwave apparatus of claim 30 further comprising, in combination: a series of subapertures located along the second waveguide conduit intermediate the first and second ends and spaced from each other in the range of one quarter wavelength of the microwave energy generated by the microwave energy generator.

32. The microwave apparatus of claim 31 wherein the guiding means results in standing waves; and wherein the communicating means includes means for selectively shifting the standing waves of the microwave energy in the second waveguide conduit between a first position to substantially communicate with the terminal aperture of the second waveguide conduit and to not communicate substantially with the series of subapertures and a second position to substantially communicate with the series of subapertures.

33. The microwave apparatus of claim 27 wherein the absorbing means comprises a reservoir of water located in the working cavity.

34. The microwave apparatus of claim 33 wherein the water of the reservoir has a surface and wherein the terminal aperture is located below the surface of the water.

35. The microwave apparatus of claim 27 wherein the working cavity includes a wall, with the absorbing means being supported on the wall, with the terminal aperture located in the range of one quarter wavelength of the microwave energy generated by the microwave energy generator from the wall.

36. Method of guiding microwave energy in a path from a microwave energy generator and into a working cavity comprising the steps of:
   a) guiding the microwave energy in a first waveguide conduit from the microwave energy generator towards the working cavity to a first point;
   b) continuously reflecting the microwave energy guided in the first waveguide conduit from the first point into a second waveguide conduit for introduction into the working cavity, with the microwave energy being reflected at an angle; and
   c) selectively shifting the angle of reflection of the microwave energy into the second waveguide conduit for shifting the standing waves in the second waveguide conduit.

37. The method of claim 36 further comprising the step of: sensing a condition; and wherein the step of shifting the angle of reflection is in response to the condition sensed.

38. The method of claim 37 wherein the step of sensing a condition comprises the step of sensing temperature in the working cavity.

39. The method of claim 36 further comprising the step of providing a terminal aperture and at least one subaperture; and wherein the step of shifting the angle of reflection comprises shifting the angle of reflection of the microwave energy for shifting the standing waves between a first position to substantially communicate with the terminal aperture and a second position to substantially communicate with the subaperture.

40. The method of claim 39 further comprising the step of trapping reflected microwave energy not absorbed by the load subjected to the microwave energy in the working cavity for preventing re-entry of the reflected microwave energy from the working cavity through the terminal aperture by providing a substance for absorbing the microwave energy adjacent to the terminal aperture.

41. The method of claim 40 wherein the step of providing a substance comprises the step of providing water adjacent to the terminal aperture for trapping reflected energy.

42. The method of claim 40 wherein the working cavity has a wall; and wherein the method further comprises: locating the terminal aperture in the range of one quarter wavelength of the microwave energy from the wall.

43. The method of claim 39 wherein the working cavity has a wall; and wherein the method further comprises the step of: angling the subaperture in a nonparallel relation with respect to the wall for communicating the standing waves at a nonperpendicular angle to the wall for preventing first order reflection of the microwave energy from re-entering the subaperture.

44. Process comprising the steps of:
a) providing a working cavity;
b) sensing a condition;
c) generating microwave energy;
d) guiding the generated microwave energy into the working cavity resulting in standing waves; and
e) shifting the standing waves in response to the condition sensed.

45. The process of claim 44 wherein the step of sensing a condition comprises the step of sensing temperature within the working cavity.

46. The process of claim 44 further comprising the step of: providing means in the working cavity for hydrating potential pathogens; wherein the step of shifting the standing waves comprises the step of shifting the standing waves between a first position for direct communication with the hydrating means in the working cavity and a second position for direct communication with the working cavity.

47. Process comprising the steps of:
a) providing a working cavity having a wall;
b) generating microwave energy; and
c) guiding the generated microwave energy into the working cavity at the wall of the working cavity at a nonperpendicular angle to the wall to prevent first order reflection of the microwave energy off the wall from being reflected straight back towards the microwave energy generation.

48. The process of claim 47 wherein the guiding step comprises the steps of: providing a microwave waveguide for guiding the generated microwave energy into the working cavity through an introduction aperture; and misaligning the introduction aperture of the microwave waveguide in a nonparallel relation with respect to the wall of the working cavity to prevent first order reflection of the microwave energy off the wall from re-entering the microwave waveguide.

* * * * *

UNITED STATES PATENT AND TRADEMARK OFFICE
CERTIFICATE OF CORRECTION

PATENT NO. : 4,861,956
DATED : August 29, 1989
INVENTOR(S) : Calice G. Courneya

It is certified that error appears in the above-identified patent and that said Letters Patent is hereby corrected as shown below:

Column 2, line 40, cancel "covity" and substitute therefor --cavity--.

Column 2 line 60, cancel "2-2" and substitute therefor --3-3--.

Column 5, line 25, after "cavity" insert --9--.

Column 6, line 1, after "cavity" insert --9--.

Column 9, lines 45 and 46, cancel "and wherein;" and substitute therefor --; and wherein--.

Column 11, line 22, cancel "of".

Signed and Sealed this

Thirty-first Day of July, 1990

*Attest:*

HARRY F. MANBECK, JR.

*Attesting Officer*   *Commissioner of Patents and Trademarks*